(12) United States Patent
Sackner et al.

(10) Patent No.: US 8,790,272 B2
(45) Date of Patent: Jul. 29, 2014

(54) METHOD AND SYSTEM FOR EXTRACTING CARDIAC PARAMETERS FROM PLETHYSMOGRAPHIC SIGNALS

(75) Inventors: Marvin Sackner, Miami Beach, FL (US); Lance Myers, Ventura, CA (US); Desmond B. Keenan, Sherman Oaks, CA (US); Dana Michael Inman, Gainsville, FL (US)

(73) Assignee: adidas AG, Herzogenaurach (DE)

( * ) Notice: Subject to any disclaimer, the term of this patent is extended or adjusted under 35 U.S.C. 154(b) by 1876 days.

(21) Appl. No.: 11/753,337

(22) Filed: May 24, 2007

(65) Prior Publication Data
US 2008/0027341 A1  Jan. 31, 2008

Related U.S. Application Data

(63) Continuation-in-part of application No. 10/886,994, filed on Jul. 8, 2004, now Pat. No. 7,604,603, which is a continuation-in-part of application No. 10/107,078, filed on Mar. 26, 2002, now Pat. No. 6,783,498, application No. 11/753,337, which is a continuation-in-part of application No. 10/991,877, filed on Nov. 18, 2004, now Pat. No. 8,137,270.

(60) Provisional application No. 60/808,429, filed on May 24, 2006, provisional application No. 60/523,495, filed on Nov. 18, 2003, provisional application No. 60/586,347, filed on Jul. 8, 2004.

(51) Int. Cl.
*A61B 5/08* (2006.01)
*A61B 5/085* (2006.01)
*A61B 5/0456* (2006.01)

(52) U.S. Cl.
USPC ............................ 600/534; 600/513; 600/535

(58) Field of Classification Search
USPC .......................................... 600/534, 535, 513
See application file for complete search history.

(56) References Cited

U.S. PATENT DOCUMENTS

| | | | |
|---|---|---|---|
| 4,016,868 A | 4/1977 | Allison | 128/2.1 |
| 4,308,872 A | 1/1982 | Watson et al. | 128/725 |

(Continued)

FOREIGN PATENT DOCUMENTS

| | | |
|---|---|---|
| WO | WO 97/47236 | 12/1997 |
| WO | WO 00/71027 | 11/2000 |

(Continued)

OTHER PUBLICATIONS

Keenan, D.B. et al., "Adaptive Filtering of Heart Rate Signals for an Improved Measure of Sympathovagal Balance," Jan. 1, 2005, 8 pages.

(Continued)

*Primary Examiner* — Tammie K Heller
(74) *Attorney, Agent, or Firm* — Sterne, Kessler, Goldstein & Fox P.L.L.C.

(57) ABSTRACT

A method for determining cardiac parameters of a subject includes receiving a signal from a thoracocardiograph (TCG) sensor. The signal is sensitive to positions and/or motions of an anterior chest wall of the subject and include a cardiac component, a respiratory component, and noise and/or artifact components. The method also includes receiving one or more electrocardiogram (ECG) signals and filtering the received TCG signal to limit one or more of the respiratory component and the noise and/or artifact components. The filtering includes one or more of wavelet de-noising, non-linear filtering, and state space filtering. The method further includes ensemble averaging thefiltered TCG signal. Ensemble members are triggered by occurrence of one or more selected fiducial points determined in the ECG signal. Additionally, the method includes extracting parameters of cardiac functioning from the ensemble averaged signal.

12 Claims, 6 Drawing Sheets

(56) References Cited

U.S. PATENT DOCUMENTS

| | | | |
|---|---|---|---|
| 4,373,534 A | 2/1983 | Watson | 128/725 |
| 4,433,693 A | 2/1984 | Hochstein | 128/721 |
| 4,452,252 A | 6/1984 | Sackner | 128/671 |
| 4,456,015 A | 6/1984 | Sackner | 128/721 |
| 4,648,407 A | 3/1987 | Sackner | 128/721 |
| 4,753,088 A | 6/1988 | Harrison et al. | 525/73 |
| 4,777,962 A | 10/1988 | Watson et al. | 600/529 |
| 4,800,495 A | 1/1989 | Smith | 364/413.03 |
| 4,807,640 A | 2/1989 | Watson et al. | 600/534 |
| 4,815,473 A | 3/1989 | Watson et al. | 600/534 |
| 4,817,625 A | 4/1989 | Miles | 128/721 |
| 4,834,109 A | 5/1989 | Watson | 600/534 |
| 4,860,766 A | 8/1989 | Sackner | 600/561 |
| 4,911,167 A | 3/1990 | Corenman et al. | 600/324 |
| 4,934,372 A | 6/1990 | Corenman et al. | 600/324 |
| 4,960,118 A | 10/1990 | Pennock | 128/200.24 |
| 4,966,155 A | 10/1990 | Jackson | 128/671 |
| 4,986,277 A | 1/1991 | Sackner | 600/485 |
| 5,007,427 A | 4/1991 | Suzuki et al. | 128/659 |
| 5,040,540 A | 8/1991 | Sackner | 600/485 |
| 5,074,129 A | 12/1991 | Matthew | 66/192 |
| 5,159,935 A | 11/1992 | Sackner et al. | 600/534 |
| 5,178,151 A | 1/1993 | Sackner | 600/485 |
| 5,224,479 A | 7/1993 | Sekine | 600/389 |
| 5,301,678 A | 4/1994 | Watson et al. | 600/534 |
| 5,331,968 A | 7/1994 | Williams et al. | 600/534 |
| 5,348,008 A | 9/1994 | Bornn et al. | 600/301 |
| 5,353,793 A | 10/1994 | Bornn et al. | 600/386 |
| 5,416,961 A | 5/1995 | Vinay | 600/523 S |
| 5,447,164 A | 9/1995 | Shaya et al. | 128/710 |
| RE35,122 E | 12/1995 | Coreman et al. | 128/633 |
| 5,533,511 A | 7/1996 | Kaspari et al. | 128/672 |
| 5,544,661 A | 8/1996 | Davies et al. | 128/700 |
| 5,564,429 A | 10/1996 | Bornn et al. | 128/696 |
| 5,584,295 A | 12/1996 | Muller et al. | |
| 5,588,425 A | 12/1996 | Sackner et al. | 600/523 |
| 5,820,567 A | 10/1998 | Mackie | 600/519 |
| 5,913,830 A | 6/1999 | Miles | 600/535 |
| 5,991,922 A | 11/1999 | Banks | 2/69 |
| 6,002,952 A | 12/1999 | Diab et al. | |
| 6,015,388 A | 1/2000 | Sackner et al. | 600/529 |
| 6,018,677 A | 1/2000 | Vidrine et al. | 600/520 |
| 6,047,203 A | 4/2000 | Sackner et al. | 600/388 |
| 6,066,093 A | 5/2000 | Kelly et al. | 600/386 |
| 6,067,462 A | 5/2000 | Diab et al. | 600/310 |
| 6,223,072 B1 | 4/2001 | Mika et al. | 600/510 |
| 6,254,551 B1 | 7/2001 | Varis | 600/595 |
| 6,261,238 B1 | 7/2001 | Gavriely | 600/532 |
| 6,341,504 B1 | 1/2002 | Istook | 66/172 E |
| 6,361,501 B1 | 3/2002 | Amano et al. | 600/500 |
| 6,413,225 B1 | 7/2002 | Sackner et al. | 600/529 |
| 6,436,057 B1 | 8/2002 | Goldsmith et al. | 600/586 |
| 6,449,504 B1 | 9/2002 | Conley et al. | 600/523 |
| 6,506,153 B1 | 1/2003 | Littek et al. | |
| 6,551,252 B2 | 4/2003 | Sackner et al. | 600/536 |
| 6,604,115 B1 | 8/2003 | Gary et al. | 707/104.1 |
| 6,633,772 B2 | 10/2003 | Ford et al. | 600/345 |
| 6,699,194 B1 | 3/2004 | Diab et al. | |
| 6,702,752 B2 | 3/2004 | Dekker | 600/484 |
| 6,709,402 B2 | 3/2004 | Dekker | 600/529 |
| 6,721,594 B2 | 4/2004 | Conley et al. | 600/523 |
| 6,783,498 B2 | 8/2004 | Sackner et al. | 600/481 |
| 6,801,916 B2 | 10/2004 | Roberge et al. | 707/101 |
| 6,881,192 B1 | 4/2005 | Park | 600/529 |
| 7,001,337 B2 | 2/2006 | Dekker | |
| 7,104,962 B2 | 9/2006 | Lomask et al. | 600/529 |
| 7,604,603 B2 | 10/2009 | Sackner et al. | |
| 2002/0138014 A1* | 9/2002 | Baura et al. | 600/526 |
| 2004/0019289 A1 | 1/2004 | Ross | 600/519 |
| 2004/0249299 A1 | 12/2004 | Cobb | |
| 2005/0054941 A1 | 3/2005 | Ting et al. | 600/529 |
| 2005/0119586 A1 | 6/2005 | Coyle et al. | 600/538 |
| 2005/0228234 A1 | 10/2005 | Yang | 600/300 |
| 2008/0027341 A1 | 1/2008 | Sackner et al. | |

FOREIGN PATENT DOCUMENTS

| | | |
|---|---|---|
| WO | WO 01/25802 | 4/2001 |
| WO | WO 01/78577 | 10/2001 |
| WO | WO 2004/091503 | 10/2004 |
| WO | WO 2005/115242 A2 | 12/2005 |

OTHER PUBLICATIONS

Sagie et al., "An Improved Method for Adjusting the QT Interval for Heart Rate," (the Framingham Heart Study), The American Journal of Cardiology, vol. 70, Sep. 15, 1992, pp. 797-801.

Fahrenberg, "Origins and Developments of Ambulatory Monitoring and Assessment", in J. Fahrenberg and M. Myrtek (Eds.), pp. 587-614 (2001), Progress in Ambulatory Assessment. Seattle, WA: Hogrefe and Huber.

Gore Electronic Products, "Expanded PTFE Insulation Material", www.goreelectronics.com (visisted Aug. 2005).

Grossman, P. et al., "A Comparison of Three Quantification Methods for Estimation of Respiratory Sinus Arrhythmia", Psychophycology, vol. 27, No. 6, pp. 702-714 (1990).

Habib et al., "Microcontroller-Based Underwater Acoustic ECG Telemetry System", IEE Transactions on Information Technology in Biomedicine, vol. 1, No. 2, pp. 150-154 (Jun. 1997).

Istepanian, R.S.H. et al., "Microcontroller-Based Underwater Acoustic ECG Telemetry System," IEEE Transactions on Information Technology in Biomedicine, vol. 1, No. 2, Jun. 1997, pp. 150-154.

Keenan, D.B. et al., "Adaptive Filtering of Heart Rate Signals for an Improved Measure of Sympathovagal Balance" (unpublished).

Klabunde, R.E., "Electrocardiogram (EKG, ECG)", Cardiovascular Physiology Concepts, www.cvphysiology.com (visited Mar. 2005).

Marin, J.M. et al., "Inspiratory Capacity, Dynamic Hyperinflation, Breathlessness, and Exercise Performance During the 6-Minute-Walk Test in Chronic Obstructive Pulmonary Disease", Am. J. Respir. Crit. Care Med., vol. 163., pp. 1395-1399, (2001).

McNaughton, T.G. et al., "Metallized Polymer Fibers as Leadwires and Intrafascicular Microelectrodes", J. Neurosci. Methods, 70(1):103-10 (1996).

Micro-Coax, "About Micro-Coax", www.microcoax.com (visited Aug. 2004).

Niskanen et al., "Software for Advanced HRV Analysis", University of Kuopio Department of Applied Physics Report Series, pp. 1-11 (Feb. 2002).

O'Donnell, D. E. et al., "Dynamic Hyperinflation and Exercise Intolerance in Chronic Obstructive Pulmonary Disease", Am. J. Respir. Crit. Care Med., vol. 164, pp. 770-777, (2001).

O'Donnell, D. E., "Ventilatory Limitations in Chronic Obstructive Pulmonary Disease", Medicine & Science in Sports & Exercise, pp. S647-S655, (2001).

Park, H.J. et al., "Automated Detection and Elimination of Periodic ECG Artifacts in EEG Using the Energy Interval Histogram Method", IEEE Transactions on Biomedical Engineering, vol. 49, No. 12 pp. 1526-1533 (2002).

Pietraszek et al., "Simple Telemetry System for ECG Recording", Polish J. Med. Phys. & Eng. 2002; 8(3): 193-198.

Signal Consulting Inc., "Inductance of Circular Loop", www.sigcon.com (visited Aug. 2005).

Van Dijk et al., "Determinants of Brachial Artery mean 24 h Pulse Pressure in Individuals with Type II Diabetes Mellitus and Untreated Mild Hypertension", Clinical Science (2002), 102, pp. 177-186.

6th Portuguese Conference on Biomedical Engineering, "BioEng' 2001 Conference Papers", 5 pages (Jun. 2001).

Almeida et al., "Wavelet Transform Based Matlab System for the Detection and Delineation of QRS Complexes in Ambulatory ECG Records", 6th Portuguese Conference on Biomedic al Engineering (Jun. 2001).

Anderer, P. et al., "Artifact Processing in Computerized Analysis of Sleep EEG—A Review" Neuropsychobiology, vol. 40 pp. 150-157 (1999).

Bianchi, A.M. et al., "Extraction of the Respiration Influence From the Heart Rate Variability Signal by Means of Lattice Adaptive Filter", IEEE Transactions on Biomedical Engineering, pp. 121-122 (1994).

(56) References Cited

OTHER PUBLICATIONS

Bonnet, M. et al., "EEG Arousals: Scoring Rules and Examples—A Preliminary Report from the Sleep Disorders Atlas Task Force of the American Sleep Disorders Association", *Sleep*, vol. 15, No. 2, pp. 173-184 (1992).

Coyle, M.A. et al., "Home Measurement of Cough Indicates Circadian Frequency Pattern and Abnormal Distribution During Sleep", LifeShirt System, study sponsored by Pfizer, Inc., Jun. 2004.

* cited by examiner

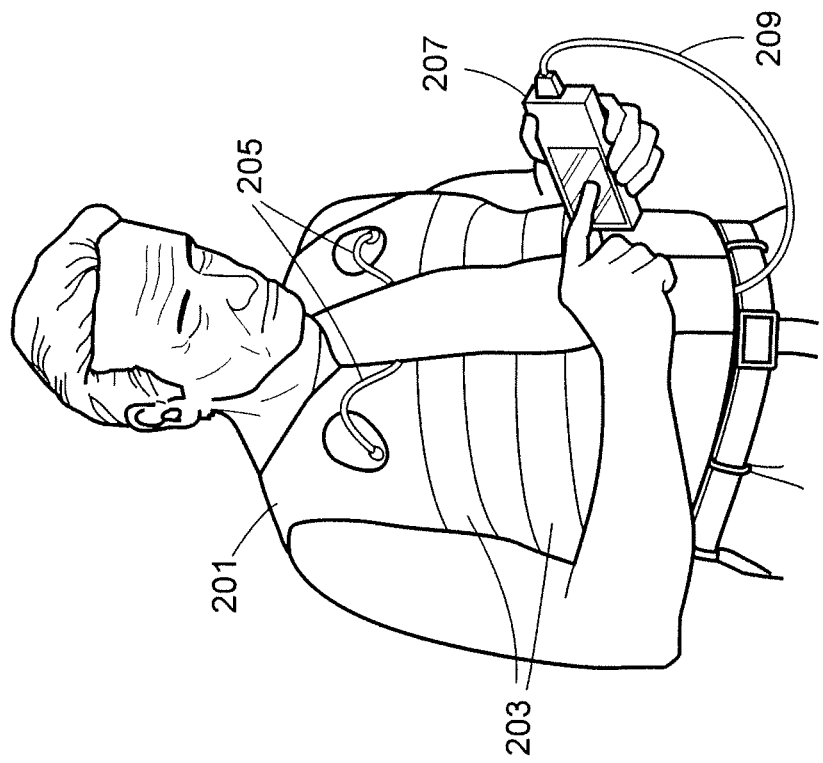
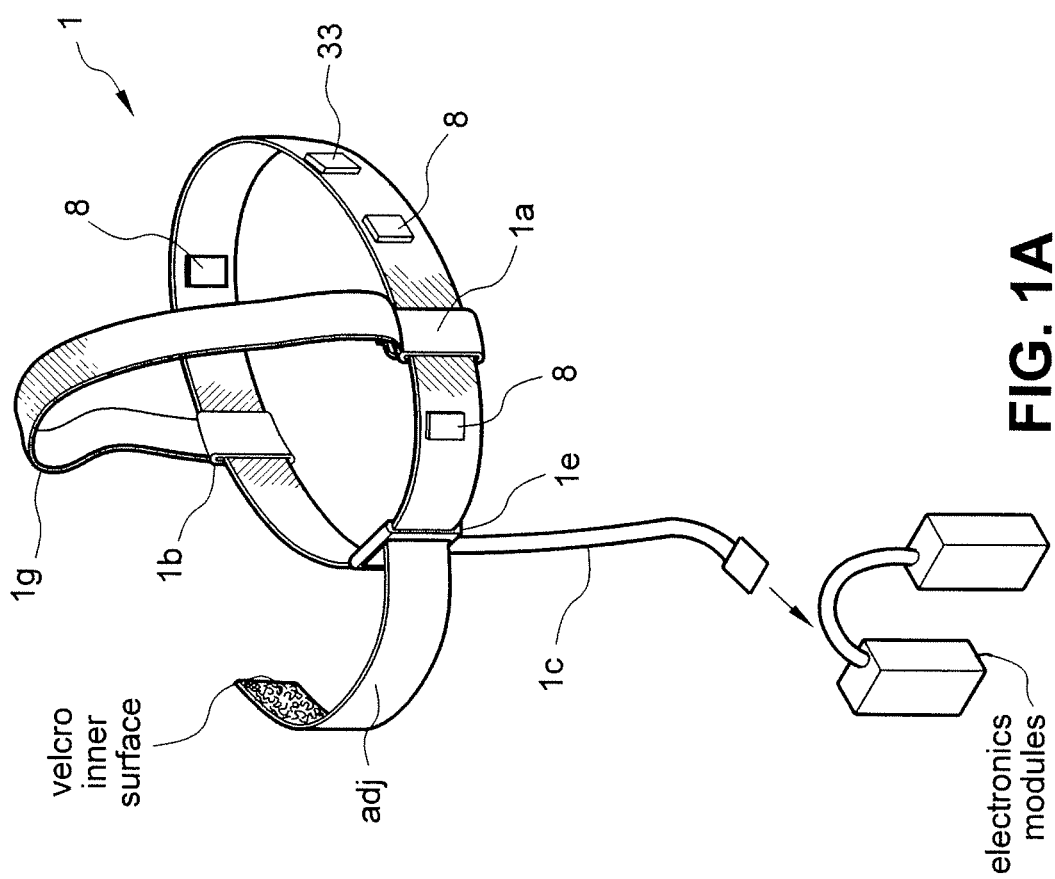
FIG. 1A
FIG. 1B

METHOD AND SYSTEM FOR EXTRACTING CARDIAC PARAMETERS FROM PLETHYSMOGRAPHIC SIGNALS

CROSS REFERENCE TO RELATED INVENTIONS

This application claims the benefit of U.S. provisional application No. 60/808,429, filed May 24, 2006; this application is also a continuation-in-part of U.S. application Ser. No. 10/886,994, filed Jul. 8, 2004, now U.S. Pat. No. 7,604,603, which is a continuation-in-part of U.S. application Ser. No. 10/107,078, filed Mar. 26, 2002, now U.S. Pat. No. 6,783,498. This application is also a continuation-in-part of U.S. application Ser. No. 10/991,877 filed Nov. 18, 2004, now U.S. Pat. No. 8,137,270, which in turn claims the benefit of U.S. provisional application No. 60/523,495 filed Nov. 18, 2003, and 60/586,347 filed Jul. 8, 2004. Application Nos. 60/808,429, 60/586,347, 60/523,495, Ser. Nos. 10/991,877, 10/886,994, now Ser. No. 10/107,078 and U.S. Pat. No. 6,783,498 are included by reference herein in their entireties for all purposes.

FIELD OF THE INVENTION

The present invention relates to the field of ambulatory and non-invasive monitoring of an individual's physiological parameters. In particular, the invention relates to an apparatus and method for extracting clinically useful cardiac signals reflecting moment-by-moment cardiac chamber volumes and cardiac blood flows that is minimally inconvenient and burdensome for a subject.

BACKGROUND OF THE INVENTION

Several cardiac parameters of clinical interest for detecting or monitoring important health conditions can only be determined from measurements of moment-by-moment cardiac chamber volumes and cardiac blood flows. For many health conditions, it is desirable that these parameters be determined from time-to-time with only minimal inconvenience and burden to a subject patient.

Several methods are known in the prior art for measuring volumes and flows many of which are inconvenient and burdensome to varying degrees. For example, volumes and flows can be determined from invasive clinical procedures, e.g., cardiac catheterization, that are best performed in operating-room-like conditions, are highly inconvenient and burdensome, can be performed only rarely, and require highly trained medical personnel. Volumes and flows can also be determined by less burdensome, non-invasive procedures, e.g., ultrasound examination, cardiac kymography (CKG, also known as displacement cardiography), and the like. However, ultrasound examination usually requires trained medical personnel and is commonly requires that the patient be at rest. CKG provides a usable output signal only when its electromagnetic field electrode has been carefully positioned near the patient's chest; the signal is lost upon any movement of the electrode.

A further non-invasive method for extracting moment-by-moment cardiac chamber volumes and cardiac blood flows is known as thoracocardiography (TCG). TCG measures the mechanical displacement of the anterior chest wall overlying the heart, and extracts from an input chest wall motion signal an output signal reflecting primarily cardiac motion. Although TCG measurements (depending on the sensor used) are at most minimally inconvenient and burdensome and do not require trained medical personnel, prior art methods and systems have had difficulty in extracting clinically useful cardiac signals. This is primarily because cardiac activity makes a very small contribution to total chest wall motion, and further because the frequencies of cardiac activity overlap the frequencies of other much larger signal components.

In more detail, the total chest wall motion signal includes components arising from motion due to respiration, from motion due to cardiac expansion and contraction, and from artifact motions due to, e.g., subject motion or equipment noise. The cardiac component has an amplitude that is at most about 1-4% of the amplitude of the respiratory component. Further, its frequency usually varies between about between about 0.8 Hz and 1.7 Hz (while resting but higher during activity) with harmonics both above and below this range, and therefore overlaps the frequency of the respiratory component which usually varies between about 0.2 Hz and about 0.5 Hz with both higher and lower harmonics. The artifact component can have unpredictable amplitude and a widely-varying frequency.

Therefore, there remains a need for less inconvenient and burdensome method for measuring moment-by-moment cardiac chamber volumes and cardiac blood flows that provides clinically useful cardiac signals.

SUMMARY OF THE INVENTION

In a preferred embodiment, the present invention provides systems for testing a subject for the presence of ischemic heart disease including a stressor for causing physiological stress in the subject; a thoracocardiograph (TCG) sensor sensitive to positions and/or motions of the anterior chest wall of the subject; an electrocardiograph (ECG) sensor; and an analysis computer for extracting cardiac parameters from TCG sensor signals by performing steps of receiving TCG and ECG signals, filtering the received TCG signals in order to enhance a cardiac component, ensemble averaging the filtered TCG signal triggered by occurrence of one or more fiducial points in the ECG signal, and extracting automatically the cardiac parameters.

In further embodiments, the provided analysis computer applies signals to the stressor that control the level of stress caused by the stressor, the control signals being determined in dependence on the extracted cardiac parameters; the provided TCG sensor includes a conductive element having electrical characteristics sensitive to positions and/or motions of the of the anterior chest wall of the subject; and electronic circuitry coupled to the conductive element, wherein the circuitry generates a changing frequency in response to changes in the electrical characteristics of the conductive element; a monitoring garment, such as a band, a shirt, a vest, and a form fitting version of a band, a shirt, or a vest, is provided for retaining the TCG sensor in operable contact with the subject;

In further embodiments, the extracted cardiac parameters include indicators of dyskinetic ventricular wall motion that signify the presence of myocardial ischemia and also signify the severity of ischemia; the provided analysis computer extracts characteristics of the ECG signal that signify the presence of myocardial ischemia; the stressor can be one of more of a graded exercise device, a pharmacological agent, and events of daily life; and the TCG signals are transmitted to the analysis computer via one or more communication links at least one of which is a wireless communication link.

In another preferred embodiment, the present invention provides automatic methods for determining cardiac parameters of a subject including receiving signals from a thoracocardiograph (TCG) sensor, the signals sensitive to positions and/or motions of the subject of the anterior chest wall of the subject, and the signals having a cardiac component, a respiratory component, and noise and/or artifact components; receiving one or more electrocardiogram (ECG) signals; filtering the received TCG signals in order to limit one or more of the respiratory component and the noise and/or artifact components, the filtering can be one or more of wavelet de-noising, non-linear filtering, and state space filtering; ensemble averaging the filtered TCG signal, ensemble members being triggered by occurrence of one or more selected fiducial points determined in the ECG signal; and extracting automatically parameters of cardiac functioning from the ensemble averaged signal.

In further embodiments, the extracted cardiac parameters can includes one or more of stroke volume, cardiac output, pre-ejection period, peak ejection rate, time to peak ejection rate, peak ejection rate divided by stroke volume, 50% filling fraction, peak filling rate, E/A ratio, deceleration time, indicators of the presence or absence of myocardial ischemia, and indicators of the severity of myocardial ischemia if present; the extracted parameters can also or alternatively include indicators of dyskinetic ventricular wall motion, so that the methods can determine whether or not myocardial ischemia is likely to be present, and if present, determining the severity of ischemia in dependence the indicators of dyskinetic motion; the methods can also determine whether or not hypovolemia is likely to be present by comparing current values of at least the stroke volume and cardiac output selected parameters with prior values of at least the stroke volume and cardiac output; and the methods can also determine whether or not congestive heart failure (CHF) is likely to be present, and if present, determining the severity of the CHF in dependence on the values of selected parameters.

In further embodiments, the fiducial points in the ECG signal selected for triggering the ensemble averaging can be one or more of the P wave, the Q wave, the R wave, the S wave, and the T wave; the method can further determine artifacts and/or noise by determining whether artifacts and/or noise are likely to be present in a signal during a period of time if either a fiducial point in an input signal that is expected to occur during the period cannot be recognized during the period, or a fiducial point occurs during the period at a time that is not expected; and excluding all signals during the period of artifacts and/or noise are likely to be present in any signal; the fiducial points in input signals can be selected from one or more of the P, Q, R, S, and T wave in an ECG signal; the extracted cardiac parameters; and features of the ventricular wall motion and its first derivative including maxima, minima, or zero crossings; and the expected occurrence time of a selected fiducial point during a period can be found in dependence on a plurality of prior occurrence times of the selected fiducial point.

In another preferred embodiment, the present invention includes provides methods of subject monitoring and of subject treatment. One provided method of treating cardiac disease includes measuring initial cardiac parameters of the subject according to the methods of claim 10 during an initial period and while the subject is performing normal daily activities; and recommending initial treatment to the subject, the initial treatment depending at least in part on the initial cardiac parameters.

In further embodiments, subsequent cardiac parameters of the subject can be measured according to the methods of claim 10 during a subsequent period and while the subject is performing normal daily activities; and further treatment can be recommended to the subject, the further treatment depending at least in part on the initial cardiac parameters, the subsequent cardiac parameters, and differences between the initial and subsequent cardiac parameters; the steps of measuring subsequent cardiac parameters and recommending further treatment can be repeated; subsequent to measuring the initial cardiac parameters, the cardiac parameters of the subject can be monitored during a plurality of time periods, the subject performing daily activities during one or more of the monitoring periods; the subject can be ambulatory while performing daily activities; and the cardiac diseases treated include myocardial ischemia, and wherein the cardiac parameters include indicators of dyskinetic ventricular wall motion.

In further embodiments, the subject's cardiac parameters can be monitored semi-continuously or continuously monitored even while performing daily activities from time-to-time or is asleep Another provided method of treating a subject monitors the subject for hypovolemia by measuring initial cardiac parameters of the subject according to the methods of claim 10 during an initial period and while the subject is performing normal daily activities the initial measured parameters are at least stroke volume and cardiac output; measuring initial cardiac parameters of the subject according to the methods of claim 10 during a subsequent period and while the subject is performing normal daily activities the initial measured parameters are again at least ing stroke volume and cardiac output; and determining the whether or not hypovolemia is present in the subject depending at least in part on the initial stroke volume and cardiac output, the subsequent stroke volume and cardiac output, and differences between the initial and subsequent stroke volume and cardiac output.

The invention are provides the following aspects. One aspect of the present invention is directed to a method for extracting cardiac parameters from a plethysmographic signal, the plethysmographic signal being responsive to at least one cardiac parameter, that performs a frequency domain filtering operation on the plethysmographic signal producing a first filtered signal; performs a time domain filtering operation on the first filtered signal, producing a second filtered signal; and extracts the cardiac parameter from the second filtered signal. The frequency domain filtering operation may include a band-pass filter and furthermore be characterized by a lower corner frequency that is determined by a heart rate. The ensemble averaging operation can include associating a plurality of segments of the plethysmographic signal with events characteristic of a cardiac cycle; shifting a plurality of segments to align the events associated with each of the plurality of events characteristic of the cardiac cycle; constructing an ensemble averaged cardiac cycle signal from the average of the plurality of aligned segments. The event characteristic of a cardiac cycle are preferably indicia derived from the electrocardiographic R-wave. The ensemble averaging operation further includes the step of reconstructing a thoracocardiograph signal from the ensemble averaged cardiac cycle signal.

Another aspect of the present invention is a method for extracting cardiac parameters from a plethysmographic signal characterized by a heart rate, the method performing the steps of: performing a first band-pass filtering operation on the plethysmographic signal producing a first filtered signal, the first filtering operation characterized by a lower corner frequency less than the heart rate; performing a second band-pass filtering operation on the plethysmographic signal producing a second filtered signal, the second filtering operation characterized by a lower corner frequency greater than the lower corner frequency of the first filtered operation; interpolating the first filtered signal and the second filtered signal based on the heart rate to produce a filtered plethysmographic signal; and extracting cardiac parameters from the filtered plethysmographic signal. Variants of the several aspects of this invention further include methods performing ensemble averaging of a signal at a current time sample by forming a weighted average of the signal at the current time sample with one or more signals at displaced time samples, the displaced time samples differing from the current time sample by one or more electrocardiographic R-wave intervals; determining R-wave intervals by detecting R waves in a concurrent electrocardiogram; and discarding a detected R wave that occurs in an ectopic temporal location or during a period of increased motion.

Further aspects of the present invention include computers, computer systems, and programmable devices for performing the methods of this invention. Further aspects of the present invention include computer readable media having encoded thereon stored instructions for causing a processor to perform the methods of this invention.

In the following, and in the application as a whole, headings are used for clarity and convenience only.

BRIEF DESCRIPTION OF THE DRAWINGS

The present invention may be understood more fully by reference to the following detailed description of preferred embodiments of the present invention, illustrative examples of specific embodiments of the invention, and the appended figures in which:

FIGS. 1A-B illustrate monitoring garments suitable for TCG measurements;

DETAILED DESCRIPTION OF THE PREFERRED EMBODIMENTS

Figure 2:
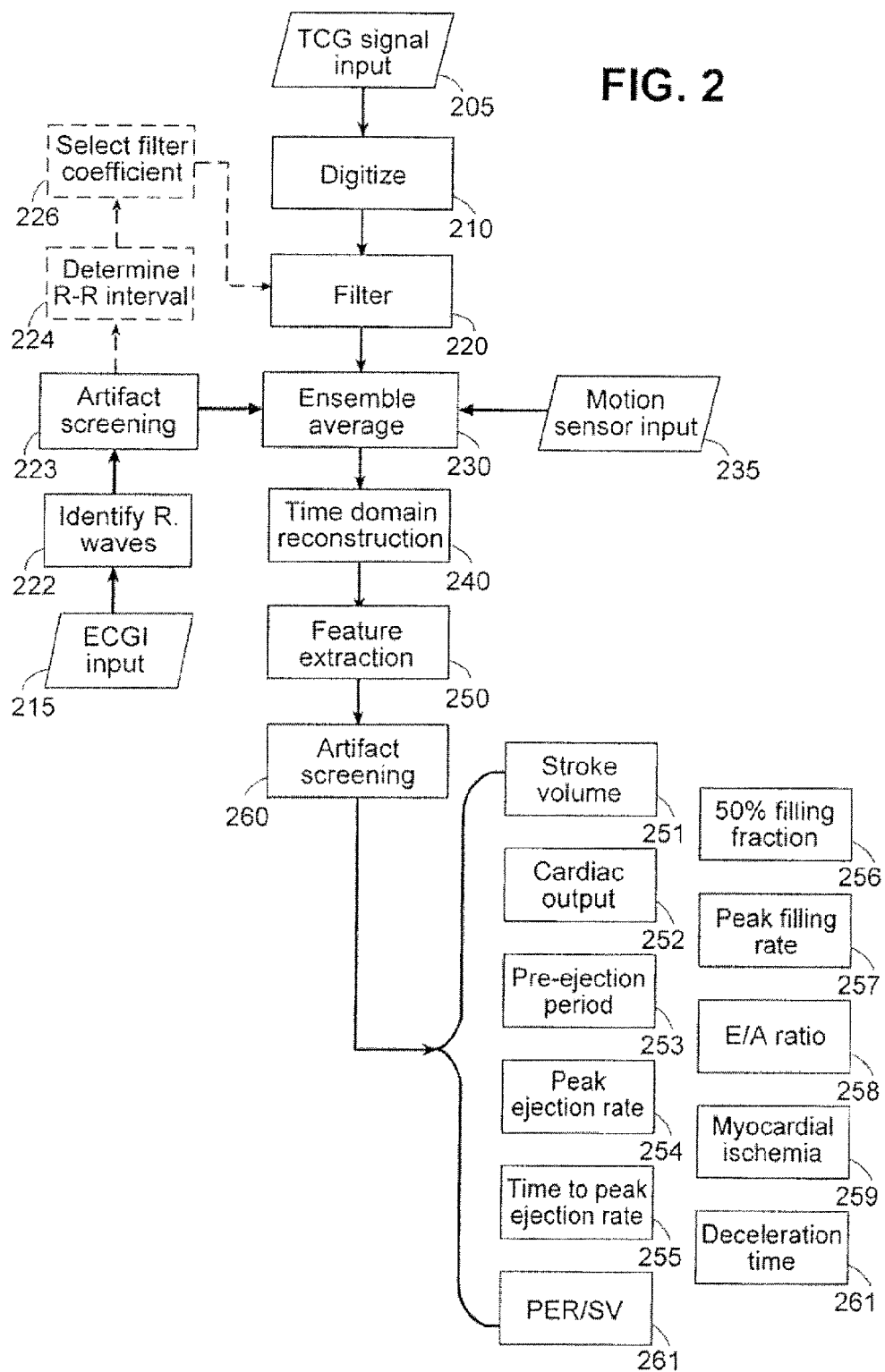
FIG. 2 illustrates a block diagram of a preferred embodiment of the present invention.

The present invention extracts cardiac signals reflecting moment-by-moment cardiac chamber volumes and cardiac blood flows from measurement of chest wall movements or pulsations. Prior to describing preferred signal extraction methods, preferred chest wall measurement techniques are reviewed.

Preferred chest-wall measurement techniques, in particular, plethysmographic techniques are minimally inconvenient and burdensome for a subject. As used herein, "plethysmography", and its derivative words, refers to the external measurement that reflects the size of an internal body part. For example, an external size of a subject's chest, e.g., its circumference, that varies with breathing reflects the internal lung volume; an external length (or circumference) along a subject's anterior, mid-thorax that changes with pulsations of the heart reflects interior cardiac volume; a circumference of a subject's arm reflects pulsations of arteries within the arm; and so forth. A "plethysmographic signal" is a signal generated by plethysmography. If the plethysmographic signal reflects internal lung volume, it is referred to as a respiratory plethysmographic signal; if the plethysmographic signal reflects internal cardiac pulsations, it is referred to as a thoracocardiographic (TCG) signal. TCG signals preferably reflect one or more anterior, mid-thorax lengths (referred to in the following as "chest lengths") or equivalent measurements.

A preferred plethysmographic technique is known as "inductive plethysmography" (IP). IP is based on determination of an inductance or a mutual inductance of an inductance sensor that is arranged to follow the expansions and contraction of a body part. The inductance sensor may be as simple as a conductive loop along a portion or all of a circumference of a body part. As the body part expands and contracts, the length of the loop (or the area enclosed by the loop) also expands and contracts thereby changing the inductance of the loop. Loop inductance changes can be converted to electrical signals using methods known to one of skill in the electrical art. The electrical signals can then be translated into physiological parameters.

In particular, in the case of the present invention it is preferred that the IP-sensor loop (or loops) be arranged at least symmetrically along the anterior portion of a chest circumference at the level of the xiphoid process (or other anatomic location responsive to cardiac pulsations). Multiple similarly placed loops can be used for increased sensitivity. If, for example, further IP-sensor loops are also placed around all or part of the chest and/or abdomen, changes in the loop inductance reflect respiratory volumes and can be converted to respiratory parameters. See, e.g., U.S. Pat. No. 4,308,872 ("'872 patent") issued Jan. 5, 1982; and co-pending U.S. app. Ser. No. 09/836,384 filed on Apr. 17, 2001

For brevity and concreteness but without limitation, the following description is largely in terms of signals obtained from the preferred inductive plethysmographic ("IP") sensor technologies. However, the signal processing and artifact rejection methods are not IP specific and can equally process signals including combinations of respiratory motions and cardiac wall motions obtained in many different ways. Thus, the invention is not limited to processing signals from IP sensors, and alternative sensor technologies that provide signals responsive to lengths, or cross-sectional areas, or circumferences, or their geometric equivalents, or measurements that can be converted into such information (for example, stress or strain of an expandable loop about the subject) are equally useful in the present invention.

Preferred processing methods described in the following also rely on electrocardiograph (ECG) signals and/or accelerometer signals that are concurrent with the chest wall motion signals. ECG signals can provide independent information on the cardiac cycle, and can be gathered as known using ECG electrodes in contact with the subject's skin. For subject comfort, preferred ECG electrodes are made of flexible, conductive cloth. Signals from one or more accelerometers can provide indicia of concurrent subject posture, motion and activity. Posture is known the modify IP signals, and posture information can be used to correct for such modification. Motion artifacts in chest wall signals are often due to subject motion, and motion and activity information can provide indicia of expected artifact levels.

For minimal subject inconvenience and burden it is usually preferably for IP-sensor loop or loops, as well as further sensors such as ECG electrodes or accelerometers, to be mounted, or attached, or integral to a close-fitting (or form fitting) garment that expands and contracts with the body cross-section. Mounting in such a garment is a convenient method for insuring that IP sensor loops closely follow expansion and contraction of the underlying body part. Garment options include a shirt, a vest, one or more bands, a chest strap, a patch, a cap, or the like, in or on which plethysmographic or physiological sensors are disposed. See, e.g., U.S. Pat. No. 6,047,203 issued Apr. 4, 2000, and U.S. Pat. No. 6,551,252 issued Apr. 22, 2003.

FIGS. 1A-B illustrate exemplary garments. FIG. 1A illustrates garment configuration 201 in the form of a flexible band of limited width and of sufficient length to encircle the torso of a monitored subject. The band includes an adjustment section ("ADJ") for retaining the band during subject activities and an active section for mounting or incorporating sensors. The adjustment section includes mating Velcro surfaces which thread through buckle 1e and which can hold the band at a tension sufficient to prevent or limit motion of the band during subject activities. Another useful adjustment feature is over-the-shoulder strap 1g which extends from anterior front buckle 1a affixed to the band, over a subject's shoulder, and to posterior rear buckle 1b affixed to the band. The active sections provide for physiological sensors. IP sensor can be mounted on or incorporated into this portion of the band. The active section can also provide for ECG electrodes 8 (preferably made of a flexible, conductive cloth); accelerometers 33, and other optional sensors.

Sensor signals are received and processed, e.g., digitized and filtered, by circuitry in the associated electronics modules carried on the band itself or on another of the subject's garments and coupled to the sensor by cable 1c. The electronic modules may also contain circuitry for storing raw and/or processed signal data on computer-readable media for later review, or alternatively, for wireless transmission of raw and/or processed signal data for immediate review.

FIG. 1B illustrates preferred garment configuration 201 in which a half-shirt, or vest, or similar, includes at least two IP sensor bands 203 along with other sensor types, principally ECG electrodes 205, and accelerometers (positioned under the anterior flap and accordingly not illustrated), and the like. Sensor bands 203 are positioned at the rib cage and abdomen to be most responsive to respiratory signals; a third IP band (not illustrated) positioned on the mid-thorax portion at the xiphoid process serves as a TCG sensor and is further sensitive to cardiac pulsations. Separate electronic module 207 processes data received from the sensors by link 209, and also provides feedback to and from a monitored. This electronic module can also provide for storing raw or for wireless transmission of raw and/or processed signal data.

Turning now to signal extraction methods, in the following the chest-wall signal input, composite signal $T_t$, to the described processing methods is modeled by the following relation:

$$T_t = T_c + T_r + N,$$

where $T_c$ is the desired signal component reflecting cardiac wall motion, $T_r$ is the signal component reflecting respiratory motions, and N represents artifacts due to measurement noise, motion, vocalizations, and the like. No a-priori distribution is assumed for the noise signal. The sample rate of the signal is preferably 200 Hz or greater. The simplest signal extraction method actually involves little or no processing at all. It is simply to record chest-wall motion only when the subject is not breathing, or breath-holding, at rest. Under these conditions, both the $T_r$ and the N components should be limited or absent, so that the $T_c$ component can be apparent without interference. See, e.g., U.S. Pat. No. 5,178,151 (included by reference herein in its entirely). However preferred embodiments of the invention implement various signal processing techniques.

FIG. 2 is a block diagram of the preferred embodiment of the present invention. Optional steps or steps needed only in certain embodiments are identified by the dashed boxes and lines. The TCG signal 205 is directed into a digitizer 210 that samples the frequency of the TCG signal and generates a digital signal representing the cross-sectional area encircled by the plethysmographic sensor. In a preferred embodiment, the TCG signal is sampled at 200 Hz although any sampling rate substantially (1.3×) greater than the Nyquist sampling rate, which is twice the highest frequency of interest (about 10 Hz) is acceptable. The harmonics of the base frequency are important to the shape of the signal and carry the information needed for analysis. The selection of the sampling rate balances the desired level of detail in the signal against the signal processing hardware constraints and costs and is known to one of skill in the art. In one embodiment, the TCG signal is quantized to a level such that the measured cross-sectional area is accurate to at least 10 ppm, more preferably to at least 5 ppm, and most preferably to 1 ppm.

The digitized TCG signal is directed to filter 220 which removes the respiratory component and passes the cardiac component. Several different filters methods are suitable, either singly or in combination, including: digital band pass filtering, adaptive filtering, wavelet de-noising, non-linear filtering, and state space filtering. First, digital band pass filtering includes a fixed digital filter of a standard type, e.g., IIR of FIR, with a low frequency cut-off equal to or greater than an average heart rate. However, a preferred digital filter has a low frequency cutoff that adaptively tracks changes in heart rate.

In detail, the filter's upper corner frequency (high frequency cut-off) is selected to minimize artifact signals arising from subject movement or noise. The inventors have discovered that increasing the upper corner frequency from 10 Hz to 30 Hz does not result in clinically apparent improvement in the cardiac signal. Therefore, in one embodiment of the present invention, the upper corner frequency of the band-pass filter may be selected in the range from 10-30 Hz. In a preferred embodiment, the upper corner frequency is about 10 Hz.

The lower corner frequency (low frequency cutoff) is dynamically adjusted according to the cardiac, or heart, rate (HR) determined, for example, from ECG electrodes 8 (FIG. 1A) or 205 (FIG. 1B). Varying the lower corner frequency according to the heart rate allows the band-pass filter to separate the cardiac signal from the pulmonary signal over a range of physical exertions by the subject. The lower corner frequency is preferably above the frequency range of the pulmonary signal (usual between 0.2-0.5 Hz, which corresponds to a respiratory rate between 10 and 30 per minute) but sufficiently below the frequency range of the cardiac signal (usually between 0.7-2.0 Hz, which corresponds to a cardiac rate between 40 and 120 per minute) to allow the cardiac signal to pass through the filter without significant distortion from the filter roll-off. If the lower corner frequency is set too low, the cardiac signal will have a larger respiratory artifact signal but if the lower corner frequency is set too high, the attenuation of part of the TCG signal will distort the TCG waveform. A range from 0.6(HR to 0.8(HR for the lower corner frequency provides a reasonable balance between cardiac signal discrimination and cardiac signal distortion. In a preferred embodiment, the lower corner frequency is dynamically adjusted to 0.7(HR.

Figure 3A:
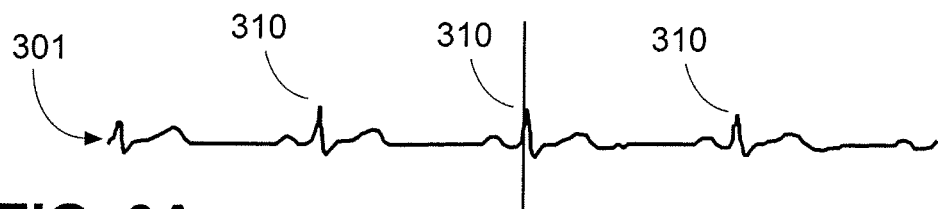
FIGS. 3A-C illustrate exemplary TCG signals.

In a preferred embodiment, R-wave occurrences (used later in ensemble averaging) and heart rate are determined 222 from the ECG signal 215 generated by the ECG electrodes mounted on the subject. R-waves are large-amplitude, short-duration pulses relative to the remainder of the ECG signal. FIG. 3a shows an ECG signal that exhibits the sharply peaked and easily identified R-waves 310 signaling ventricular depolarization. Other easily identified markers of ventricular systole may be used if available. In particular, it should be noted that determined of only R-waves alone is sufficient to determine a ventricular volume curve from TCG input signals. However, concurrent determination of P, Q, S, T waves will increase confidence and aid in rejecting artifacts.

To determine R-wave occurrences, first, candidate R-wave occurrences are identified 222 in the input ECG signals with a preferred accuracy of 1-5 msec by one of the many software methods or hardware devices known in the art, for example, by a threshold filter or other such filter known to one of skill in the art. Next, candidate R wave occurrences are screened for artifacts 423 and identified artifacts are excluded from further analysis. According to one screening method, candidate R waves are identified as artifacts if they are likely to be temporally ectopic. Candidate R waves are considered likely to be ectopic if they occur in an unexpected temporal position 426 with respect to adjacent candidate R waves by, for example, being more than approximately a selected threshold time (preferably approximately 100 msec.) either before or after an occurrence time expected in view of the recent mean heart rate. A recent mean heart rate can in turn be determined 224 from a, preferably, approximately 10 sec. running average (or other averaging times sufficient to give stable but responsive heart rates) of observed R-R intervals 224. Alternatively, the running average can include the last N (preferably 10) heart beats.

According to another perhaps more rigorous screening method, PQRST detection is performed on the ECG using known methods. If any of these fiducial points cannot be found, the current hear beat is noted as possible an artifact. Next, a running baseline median average of N (preferably 10) consecutive beats is determined for, not only RR intervals, but also for the T-wave height, P-wave height, QT interval and PR intervals. If any significant deviation of these measures occurs, the current hear beat is noted as possible an artifact. Finally, any noted cardiac cycles way are excluded from further analyses. If an ensemble average is performed, these cycles are excluded from the averages. If a time domain filtering strategy is used that uses the previous N points, these cycles are either excluded or given a lower weighting in the filtering operation. Overall this is to reduce the impact of non-sinus beats.

Further, candidate R waves are considered artifact 426 if they occur during a period of sufficiently intense subject motion. Such periods can be determined if motion sensor, e.g., accelerometer, signals 235 exceed a threshold value.

Once R-wave occurrences are identified in 222, the time interval between successive R-waves (the inverse of the heart rate) is calculated in 224. Several successive R-R intervals may be averaged to obtain a better estimate of the heart rate. In one embodiment, 15-50 R-R intervals are averaged to estimate the heart rate. In a preferred embodiment, a weighted average on a window comprising 25 R-R intervals centered on the current heart beat is used to determine the heart rate. The weights may be set equal to 1/N where N is the number of heartbeats averaged. Alternatively, the weights may be adjusted to give more weight to the heartbeats closest to the current heartbeat and less weight to the more distant (from the current heartbeat) heartbeats.

The sampled heart rate signal is converted from discrete values to a continuous time signal and low pass filtered at a sampling rate of 25 Hz as is known to one of skill in the art. The smoothing of the heart rate signal by low pass filtering reduces the discontinuities in the heart rate and in the interpolated TCG signal.

The heart rate is used to select a set of filter coefficients corresponding to a band-pass filter having a lower corner frequency closest to the calculated heart rate in 226. In order to reduce the computational load on the processor, a plurality of band-pass filters having an upper corner frequency of 10 Hz and a range of lower corner frequencies covering the expected range of heart rates are designed using tools known to one of skill in the signal processing art. For example, one such design tool is the Matlab® computer program available from The MathWorks of Natick, Mass. The sets of filter coefficients defining each band-pass filter are stored in memory for quick access by the processor. As used herein, the term processor refers to any of a type of processor commonly used by one of skill in the signal processing art and may include DSPs, FGAs, and the like. In addition, the term processor as used herein also includes supporting circuitry and components such as memory, system bus, and I/O interfaces and the like.

In one embodiment, each point of the TCG signal is an interpolation of two filters having lower corner frequencies bracketing the sampled heart rate. For example, in one embodiment, ten filters are stored in memory having lower corner frequencies from 0.4 Hz through 2.2 Hz in increments of 0.2 Hz. If the desired lower corner frequency (0.7*HR) is below 0.4 Hz, the 0.4 Hz filter is used to filter the TCG signal. Similarly, if the desired lower corner frequency is above 2.2 Hz, the 2.2 Hz filter is used to filter the TCG signal. If the desired lower corner frequency is in the range from 0.4 Hz to 2.2 Hz, the filtered TCG signal is an interpolation of the two filters bracketing the desired lower corner frequency.

In another embodiment, an interpolated filter is created and used to filter the TCG signal. The interpolated filter is created by interpolating the filter coefficients from two of the pre-designed band-pass filters stored in the processor's memory that bracket the sampled heart rate. By way of example, if the sampled heart rate of 1.0 Hz, the preferred lower corner frequency of the band-pass filter should be 0.7 Hz. If the processor has stored the filter coefficients of band-pass filters having a lower corner frequency of 0.6 Hz and 0.8 Hz, the processor creates an interpolated filter having filter coefficients given by $$\hat{\omega}_i = (1-\alpha)\omega_i^{0.6} + \alpha\omega_i^{0.8} \tag{1}$$

where $\hat{\omega}_i$ is the i-th coefficient for the interpolated filter, $\omega_i^{0.8}$ is the i-th coefficient of the pre-designed band-pass filter having a lower corner frequency below that of the desired lower corner frequency (in this example, the filter having a lower corner frequency of 0.6 Hz), $\omega_i^{0.8}$ is the i-th coefficient of the pre-designed band-pass filter having a lower corner frequency above that of the desired lower corner frequency (in this example, the filter having a lower corner frequency of 0.8 Hz), and $\alpha$ is the interpolation factor given by $$\alpha = \frac{0.7HR - lcf^+}{lcf^+ - lcf^-} \tag{1}$$

where $lcf^-$ is the lower corner frequency of the pre-designed filter below the desired corner frequency and $lcf^+$ is the lower corner frequency of the pre-designed filter above the desired corner frequency.

The computational load on the processor may be further reduced by down-sampling the digitized TCG signal prior to the band-pass filter. In one embodiment, the digitized TCG signal is re-sampled from 200 Hz to 25 Hz by performing an 8-point running average. The TCG signal is up-sampled to 200 Hz after the band-pass filter by interpolation using a spline fit to the filtered signal.

Adaptive filtering is another preferred filtering technique that can be employed at step 220 in FIG. 2. Generally, an adaptive filter removes components from a primary signal that are correlated with one or more reference signals by passing the primary signal through a filter tuned to remove frequencies present in the reference signals. Coefficients of the filter for the primary signal are selected and adjusted according to known algorithms such as Least Mean Squares (LMS), Recursive Least Squares (RLS) or Affine Projection (AP) filters. See, e.g., Haykin, *Adaptive Filter Theory*, 3rd Edition, Prentice Hall, N.J., 1996.; Widrow et al., *Adaptive Signal Processing*, New York: Prentice-Hall, 1985. Adaptive filtering coefficients can also be selected and adjusted by using neural network techniques.

Preferably signal correlated with respiration, $T_r$, can be measured by placing additional IP sensor loops about all or part of the subject's rib cage or abdomen (RIP sensors) so that they are more responsive to respiratory motions that is the TCG sensor, but are less sensitive cardiac motion than the TCG sensor. Signals correlated with motion artifact component of N can be obtained by one or more accelerometers arranged on trunk (and/or arms or legs). Using the reference signals, an adaptive filter removes the respiratory and motion artifact components, $T_r$+N, present in the input signal, $T_t$, and output primarily the cardiac component, $T_c$.

Patent application publication no US 2005/0240087 (included by reference herein in its entirely) describes in detail an implementation of adaptive filtering of chest wall signals using RIP and accelerometer reference signals.

State space filtering is a further preferred filtering technique that can be employed for filtering step 220 in FIG. 2. State space filtering estimates the state as a function of time of a discrete-time process, e.g., representing cardiac contractions, that is governed by a linear stochastic difference equation. This resulting filter then iteratively predicts the state, e.g., the degree of cardiac contraction or expansion, for each observation time and then updates its predictions based on actual measurements. See, e.g., Brown et al., 1992, *Introduction to Random Signals and Applied Kalman Filtering, Second Edition*, John Wiley & Sons, Inc.

Accordingly, the above signal model—$T_t=T_c+T_r+N$—is re-formulated in a state space representation; measurement noise, e.g., $T_r$+N, is assumed to be normally distributed with 0 mean and an estimated standard deviation; and standard Kalman filtering techniques are applied to predict $T_c(t)$. More complex, non-linear state space models, preferably employ non-linear Kalman or particle filtering to predict $T_c(t)$. A. See, e.g., Doucet et al. eds., *Sequential Monte Carlo Methods in Practice*. Springer-Verlag, New York, 2000.

Non-linear filtering is a further preferred filtering technique that can be employed for filtering step 220 in FIG. 2. Here the process generating the signal, e.g., cardiac contractions and expansions, is assumed to be non-linear. Then, noise reduction and/or signal separation is usually difficult to accomplish with traditional linear spectral approaches since, e.g., the signals may exhibit broad frequency spectra. The theory of nonlinear dynamical systems, or chaos theory, provides alternative methods for these purposes based on a phase space representation of the data. The theory behind these methods is outlined in. See, e.g., Kantz et al., Nonlinear noise reduction: a case study on experimental data, Phys. Rev. E 48 (1993) 1529; Grassberger et al., "On noise reduction methods for chaotic data", Chaos 3 (1993) 127; Schreiber, Extremely simple nonlinear noise reduction method, Phys. Rev. E 47 (1993) 2401. Non-linear filtering methods can give superior results in situations even in the absence of determinism because non-deterministic systems can exhibit structures suitable for filtering purposes when represented in a lower dimensional phase space Preferably, non-linear filtering uses delay-time embedding to create a phase space representation of measured cardiac activity, the TCG signal or $T_t$, which is a multi-dimensional attractor of this activity. Nonlinear signals will tend to form curved structures in delay space, and in particular, noisy deterministic signals form smeared-out lower dimensional manifolds. Nonlinear phase space filtering then identifies such structures onto which the input signal is projected in order to reduce noise. Thus, the non-linear noise reduction method includes the following steps: find a low dimensional approximation to the "attractor" described by the trajectory of cardiac activity; project each point in an input signal orthogonally onto the approximation to the attractor to produce a cleaned vector; and convert the sequence of cleaned vectors back into the scalar time domain to produce the output, cleaned time series. This approach has had considerable success in filtering of electrocardiogram signals which characteristics similar to TCG signals. See, e.g., Schreiber et al., Nonlinear noise reduction for electrocardiograms, CHAOS 6 (1996) 87.

Wavelet de-noising is a further preferred filtering technique that can be employed for filtering step 220 in FIG. 2. Wavelet de-noising focuses primarily on suppressing the noise part, N, of the input signal, e.g., the TCG signal or $T_t$, and to output a noise free signal, e.g., a $T_c+T_r$ signal. The method is efficient for processes that can be represented using only a few nonzero wavelet coefficients, that is for processes having a sparse wavelet representation. Viewed statistically, wavelet de-noising is a regression model over time that can be viewed as a nonparametric estimation of the function using an orthogonal basis. The wavelet method includes the following steps: decompose the input signal by computing the wavelet decomposition of the signal at a chosen level N; threshold wavelet coefficients by selecting a soft or hard threshold the coefficients at each level from 1 to N−1; reconstruct and output signal by computing wavelet reconstruction by using the thresholded detail coefficients from levels 1 to N−1 and the original coefficients at level N. See, e.g., Donoho et al, 1994, Ideal de-noising in an orthonormal basis chosen from a library of bases, CRAS Paris, Ser I, t. 319, pp. 1317-1322.; Donoho, 1995, De-Noising by soft-thresholding, IEEE Trans. on Inf. Theory, vol. 41, 3, pp. 613-627.

Although band-pass filtering 220 removes most of the respiratory component from the TCG signal, the filtered signal still contains a respiratory artifact that affects the accuracy of the extracted cardiac features. In order to reduce the respiratory artifact to a level sufficient for accurate and automatic extraction of cardiac features during normal activities of daily living, a time domain filter is used to "smooth" the TCG signal. The band-pass filtered signal is thus next directed to a time-domain averaging filter 230 that performs an ensemble average on the band-pass filtered signal. See, e.g., U.S. Pat. Nos. 5,178,151 and 6,783,498 and application publication no. US 2006/0036183.

The time-domain averaging filter 230 uses the R-wave signal 222 from the ECG electrode as a "clock" to indicate the same point in time relative to each cardiac cycle. The TCG component representing the cardiac signal will be correlated to the R-wave "clock" whereas the remaining components of the TCG signal, such as the respiratory component, will not be correlated to the R-wave "clock." The averaging filter 230 averages segments of the filtered TCG signal corresponding to a cardiac cycle, delimited by the R-wave "clock", by time shifting each cardiac cycle such that the R-wave for each cardiac cycle is aligned. The filter takes the average of several aligned cycles at each point along the cycle. Equation 1 describes the mathematical operation of the filter.

$$\hat{f}(n, t) = \sum_{i=-W}^{i=+W} w_i f(t + (R_{n+i} - R_n)) \qquad (2)$$

In equation 1, $\hat{f}(n, t)$ is the ensemble averaged signal for the n-th cardiac cycle as a function of time, t, f(t) is the (frequency-domain) band-pass filtered TCG signal, $R_n$ is the time of the n-th cardiac cycle R-wave, $w_i$ are the cycle weights, and 2W+1 is the ensemble size.

The "beginning" and "end" of a cardiac cycle referenced to the R-wave "clock" may be determined to give clinically useful data. In a preferred embodiment, a cardiac cycle "begins" at approximately 20% of the R-R period before the R-wave and ends at approximately 80% of the R-R period after the R-wave. The cardiac component of the TCG signal will "reinforce" each other because they are correlated to the R-wave "clock. The respiratory component, however, will tend to cancel out because it is not correlated to the R-wave "clock".

The size of the ensemble or the number of cardiac cycles averaged should be large enough to allow the non-stationary (not correlated to the R-wave) components to average to zero or to an insignificant level, but small enough to remain responsive to changes in cardiac activity. The ensemble size may be between 20 beats and 500, preferably between 25 or 50 beats and 250 beats and most preferably approximately 100 or 150 beats (where W=75). The ensemble size may also be adjusted to higher or lower values depending on, for example, the physical exertion of the person. Preferably, if it is known that the non-stationary components have a greater presence in an TCG signal, then longer ensemble averages are advantageous to eliminate these artifacts, for example, 200, 250, and to 500 beat ensemble averages. If the contrary is known, then shorter ensemble averages are advantageous to preserve greater detail in the cardiac signal, for example, 100, 50, and down to 25 beat ensemble averages.

Optional motion sensors, such as accelerometers 26 and 26a in FIG. 1A, may be used, in optional step 235, to provide information about the extent of subject motion and current posture that can be used in this adjustment of W. The respiratory sensor may be used to provide information about the amplitude of respiration, such as subject breath holding, that may also be used for adjustment of W.

The cycle weights, $w_i$, may be set to 1/(2W+1) for a simple average. Preferably, $w_i$ may be adjusted to give more weight to the cardiac cycles closer to the current cardiac cycle and less weight to the cycles more distant (in time) from the current cardiac cycle. More preferably, $w_i$ may be adjusted by means of the previously described tools so that, when considered as defining a standard digital filter (the "equivalent" filter) operating on a signal sampled at a fixed time increment instead of relative to the R-wave clock, they define a low-pass equivalent filter with a narrow pass band and maximum stop band attenuation. Thereby, the cardiac signal, which is substantially constant (or has substantially zero frequency) at times fixed relative to the R-wave clock, may be filtered from the respiratory and other components, which are not constant with respect to times fixed relative to the R-wave (or have non-zero frequencies).

However, the pass band of the equivalent, low pass filter defined by $w_i$ should not be so narrow as to cause loss of clinically useful cardiac information. Most preferably, then $w_i$ define an equivalent low pass filter, perhaps adjusted separately for each subject according to the subject's observed cardiac performance. Simply stated, the ensemble weights also serve to soften the onset of large "step" transition artifacts which pass the bandpass filter. As the step transition is rising slowly through the weights, other artifacts tend to cancel it before it achieves significant amplitude. Without the softening of the filter weights, the step would appear all at once, then be slowly "knocked back down" by canceling artifacts as they happen.

The TCG signal is reconstructed in step 240 by "stitching together" the ensemble averaged signal (where each output cardiac cycle is the ensemble average of (2*W+1) bandpass filtered, raw TCG signals). For example, the beginning of the n-th ensemble averaged cardiac cycle is stitched to the ending of the (n−1)-th ensemble average cardiac cycle and the ending of the n-th ensemble averaged cardiac cycle is stitched to the beginning of the (n+1)-th ensemble averaged cardiac cycle. Any discontinuities between successive cycles are smoothed by performing a preferably linear interpolation between the two successive cycles over a transition region. In one embodiment, the transition region is between 10 and 30% of the cardiac period and in a preferred embodiment, the transition occurs over 20% of the cardiac period. Also, non-linear interpolation, such as spline interpolation and least square error fits may be used.

Alternatively, ensemble averaging may be performed directly without stitching by determining an ensemble averaged signal, $\hat{f}(\ )$, at a particular time sample, t, having a nearest R wave, $R_0$, simply as the weighted average of the signals at time samples that are displaced from time sample t by R-wave intervals, that is by the intervals between $R_0$ and its adjacent R waves. Equation (3a) represents such an embodiment of such a ensemble average:

$$\hat{f}(t) = \sum_{i=-W}^{i=+V} w_i f(t + R_i - R_0) \qquad (3a)$$

Here, $R_0$ is the R wave occurrence nearest to time sample t; $R_1$ to $R_V$ are the V future R waves nearest to $R_0$; $R_{-1}$ to $R_{-W}$ are the W previous R waves nearest to $R_0$; and V and W need not be equal. The weights, $w_i$, may by fixed or variable.

Figure 3B:
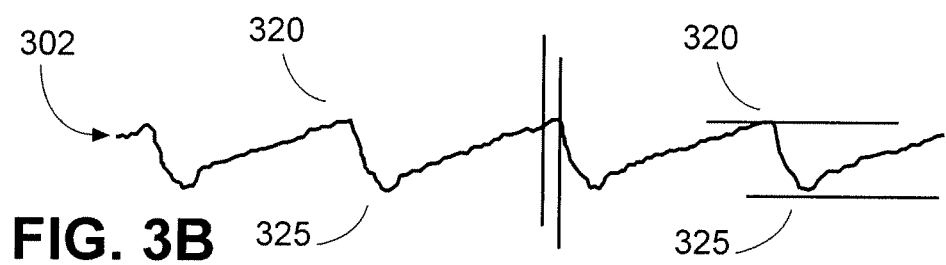
Figure 3C:
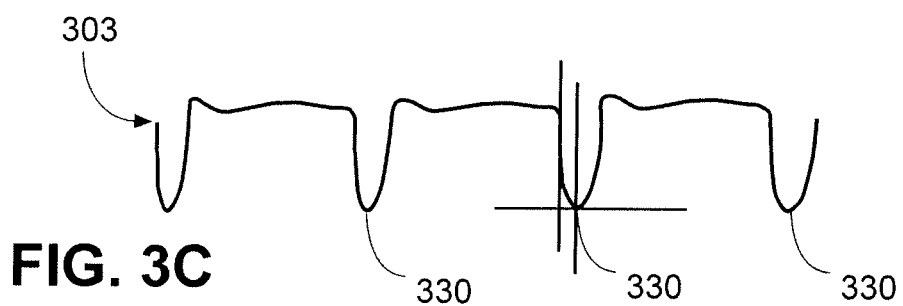

Once the time domain reconstruction (if needed) is completed, the extracted cardiac signal may be stored for later use or directly output for current use, uses including manual examination by health care personnel or others, further processing optionally in combination with other physiological signals such as, for example, the ECG and the like. One preferred use is automatic cardiac feature extraction 250 performed on the processed TCG signal. FIGS. 3a-c shows the ECG 301, processed TCG 302, and the processed TCG derivative 303 signals aligned temporally and shows certain cardiac features for each cardiac cycle extracted from the processed TCG signal.

The derivative of the processed TCG signal 303 is generated from the processed TCG signal 302 using any of the common techniques for differentiating a signal known to one of skill in the art. The times of local maximums and minimums of the TCG signal 302 may be determined by locating the zero-crossing of the derivative signal 303 through the x-axis 335 or by other methods known to those of skill in the art. After the minimums and maximums in signals 302 and 303 are identified, the cardiac parameters are determined by the processor and may be stored for later evaluation or displayed for evaluation. Features that may be extracted include but are not limited to the following, which are discussed in groups relating to systolic function, diastolic function, and myocardial ischemia.

Figure 4A:
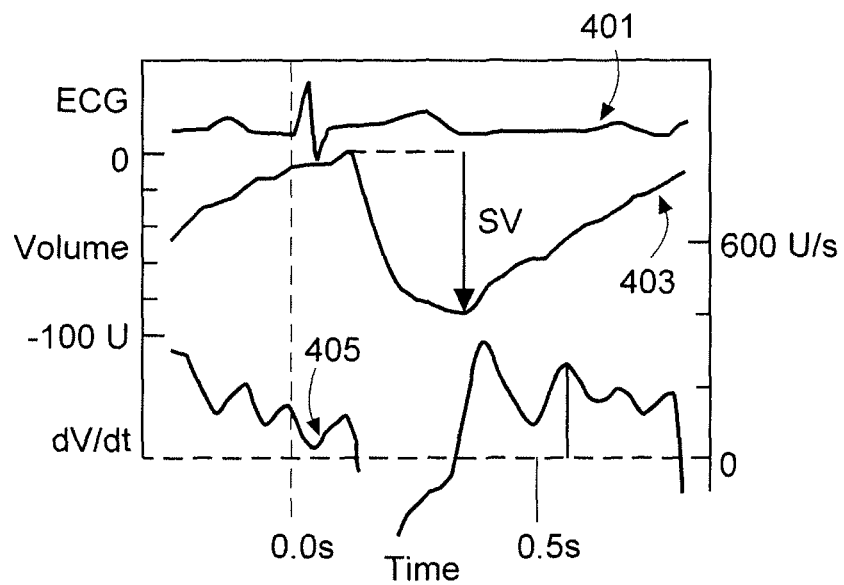
FIGS. 4A-C illustrate additional exemplary TCG signals.
Figure 4B:
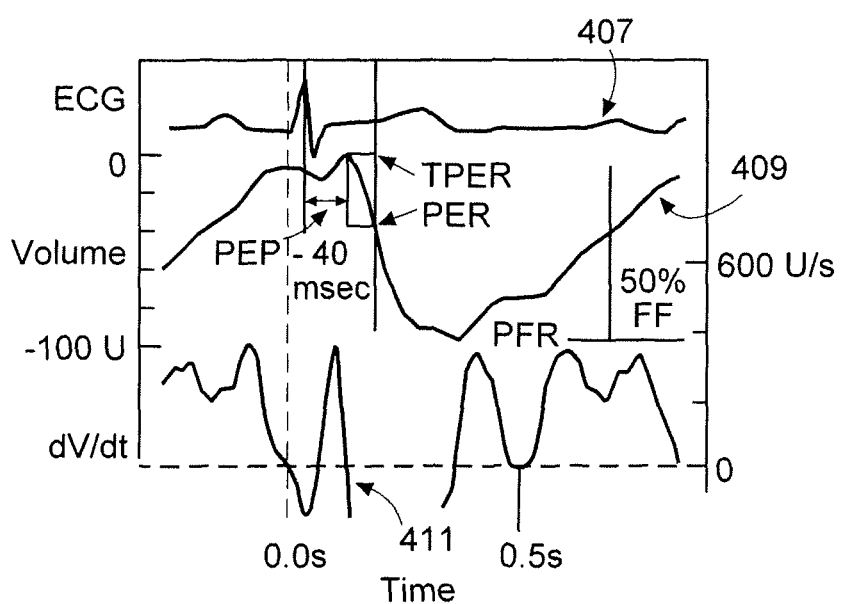

FIG. 4A illustrates, for one heart beat, an actual ECG signal 401, an actual ventricular volume signal 403 derived from a TCG signal, and an actual derivative of the ventricular volume signal 405. FIG. 4A similarly illustrates ECG signal 407, ventricular volume signal 409, and derivative of the ventricular volume signal 411. On both FIGS. 4A-B definitions of various indicia of cardiac functioning are indicated.

In addition to the derivative of the ventricular volume signal 405, any of the following indices of systolic function can be determined from the ventricular volume signal. Stroke Volume (SV) 251 is generally defined as the amplitude of the rapid ejection phase of ventricular volume waveform is proportional to stroke volume. Absolute calibration in volume units such as ml of TCG results cannot be obtained without an independent calibration method. However, reliable tracking of changes of stroke volume can be accomplished with an un-calibrated signal. SV is computed from the ventricular volume curve as the amplitude from the beginning to the end of ventricular ejection. This is defined as the segment from the onset of the major negative, systolic deflection of the ventricular volume curve to its absolute minimum. In FIG. 3B, the stroke volume indicia (SV) 251 is the amplitude from the maximum 320 of the processed TCG sample to the next minimum 325 of the processed TCG signal 302. In FIG. 4A, SV is indicated by "SV" marking the amplitude on curve 403 from the beginning to the end of ventricular ejection.

Cardiac output (CO) 252 is generally defined as the product of the stroke volume and the heart rate (CO=SV(HR). As with SV, absolute calibration requires an independent calibration method, although reliable tracking of changes of stroke volume can be accomplished with an un-calibrated signal.

SV and CO have been discovered by the inventors to be sufficiently accurate relative indicia of these cardiac parameters to be useful in clinical applications. Where a calibration has been measured relating the processed TCG signal to the actual cardiac volume, it may be used to obtain the actual SV and CO.

Peak Ejection Rate (PER) 254 is generally defined as the minimum 330 of the processed TCG derivative signal 303. In the presence of normal ejection fraction, peak ejection rate closely correlates with stroke volume and may therefore be a more reliable reference for changes in dynamics of ejection than left ventricular end-diastolic volume. This correlation of PER and SV may be used to validate changes of stroke volume.

Peak Ejection Rate/Stroke Volume (PERSV) 261 is generally defined as the ratio of peak ejection rate normalized to stroke volume and provides an indicia that is independent of calibration of stroke volume. Trends showing a decrease of PERSV imply depression of systolic function and trends showing an increase are consistent with improved systolic function. Exercise which is associated with increased stroke volume may elevate PERSV.

Time to Peak Ejection Rate (TPER) 255 is generally defined as the interval from the initiation of the decrease of the ventricular volume curve to the time of the PER as measured from the first derivative of the ventricular volume trace. In FIG. 3C, TPER is the time from the maximum 320 of the processed TCG signal 302 to the Peak Ejection Rate (PER) 330. Shortening of TPER signifies improved systolic function. Lengthening indicates depressed systolic function and may occur in the absence of change in left ventricular ejection fraction. Shortening of TPER is normally associated with aerobic exercise.

Pre-ejection Period (PEP) 253 is generally defined as the time interval from the ECG Q-wave to ejection onset in the TCG curves. Alternatively, as illustrated in FIG. 3B, PEP 253 is the time from the R-wave peak 310 to the maximum 320 of the processed TCG signal 302. PEP measured by TCG correlates well with pre-ejection period measured by applanation tonometry or phonocardiography.

PEP 253 decreases with increasing sympathetic activity as in exercise or mental stress. Also, variations of PEP with respiration during mechanical ventilation reflect fluid responsiveness: the greater the difference in PEP between inspiration and expiration, the greater the chances of volume or blood loss. Further, differences in PEP during respirations also correlate with stroke volume, e.g., the greater the difference the lower the stroke volume. PEP can serve as a marker of signal quality: excessively low or negative values or excessively high values can indicate invalid data or dyskinetic motion of the ventricle. Thus, PEP can be utilized to help determine artifacts as a component of the TCG software.

Turning to indicia of diastolic function, it is known that multiple factors contribute to diastolic filling during rest or exercise including myocardial relaxation, left atrial pressure or preload, compliance of the left ventricle, and atrial contraction. Volume, flow, and timing measures of the ventricular volume waveform during diastole can provide information regarding myocardial relaxation and left ventricular compliance. In particular, the first derivative of the TCG reflects the characteristics of left ventricular filling in a manner similar to Doppler echocardiography. Any of the following indicia of diastolic function can be determined from the ventricular volume curve.

The 50% Filling Fraction (FF50) 256 is the duration during diastole measured on the ventricular volume curve from end-systolic time to the time at which 50% filling occurs (other filling fractions, e.g., 33% or peak filling time are measured at the times of other fractional filling). After these points are located on the ventricular volume curve, values from end-systole upwards to end-diastole are computed which is then divided by stroke volume.

TCG measurements of FF50 reveal that this value significantly increases when healthy subjects are fluid loaded with intravenous saline. The FF50 decreases in the presence of blood and fluid losses. In patients with hypertension, FF50 increases within three to six months following successful treatment.

Peak Filling Rate (PFR) 257 is the greatest rate of increase of the ventricular volume signal, or in other words, the diastolic maximum value of the first derivative of the ventricular volume curve. PFR correlates to the E wave of echo-Doppler trans-mitral blood flow but differs because PFR is the first derivative of changes of total ventricular blood volume. In patients with hypertension, PFR increases within three to six months after successful treatment.

E/A ratio (E/A) 258 is determined from the identified E and A these waves in the first derivative of the ventricular volume curve in the following manner. Diastole is first identified; and then the two principal maxima in the first derivative of the ventricular volume signal after the peak of the ECG T-wave are found. The first peak is due to untwisting of the ventricle, while the second peak is the "E" wave due to rapid filling of the ventricle. The A-wave is identified as the peak of the derivative immediate preceding the R-Wave (and is not time adjusted since it is compared to the E-wave of the ventricular volume curve not an electrical signal) The peak of the "E"-wave is divided by the peak of the "A"-wave to provide a dimensionless value for the "E/A" ratio.

Deceleration time (DT) 262 is generally defined as the time from the peak of the "E" wave to the baseline of the ventricular volume curve.

Indicia of myocardial ischemia (259) can also be automatically derived from the ventricular volume curve; especially from it's over shape during systole. Myocardial ischemia can occur as a result of increased myocardial oxygen demand, reduced myocardial oxygen supply, or both. In the presence of coronary artery obstruction, an increase of myocardial oxygen demand caused by stressors such as exercise, tachycardia, or emotion can lead to a transitory imbalance in oxygen supply and demand. This condition, often referred to as demand ischemia, is responsible for most episodes of chronic stable angina. In other situations, the imbalance is caused by an acute reduction of oxygen supply secondary to, e.g., increased coronary vascular tone (i.e., coronary vasospasm) or by marked reduction or cessation of coronary flow due to, e.g., of platelet aggregates, thrombi, and the like. This condition, often referred to as supply ischemia, is responsible for many instances of myocardial infarction (MI) and for most instances of unstable angina (UA). And, in many other conditions, myocardial ischemia results from both an increase in oxygen demand and a reduction in supply.

Myocardial ischemia may be symptomatic or silent. Silent myocardial ischemia is indicated by lack of symptoms apparent to a subject in the presence of documented evidence of myocardial ischemia from, e.g., ECG, nuclear imaging, or the like. Included are subjects who truly have no symptoms alone with subjects with only subtle evidence of coronary heart disease (CHD), e.g., decreased endurance or energy without pain.

Figure 4C:
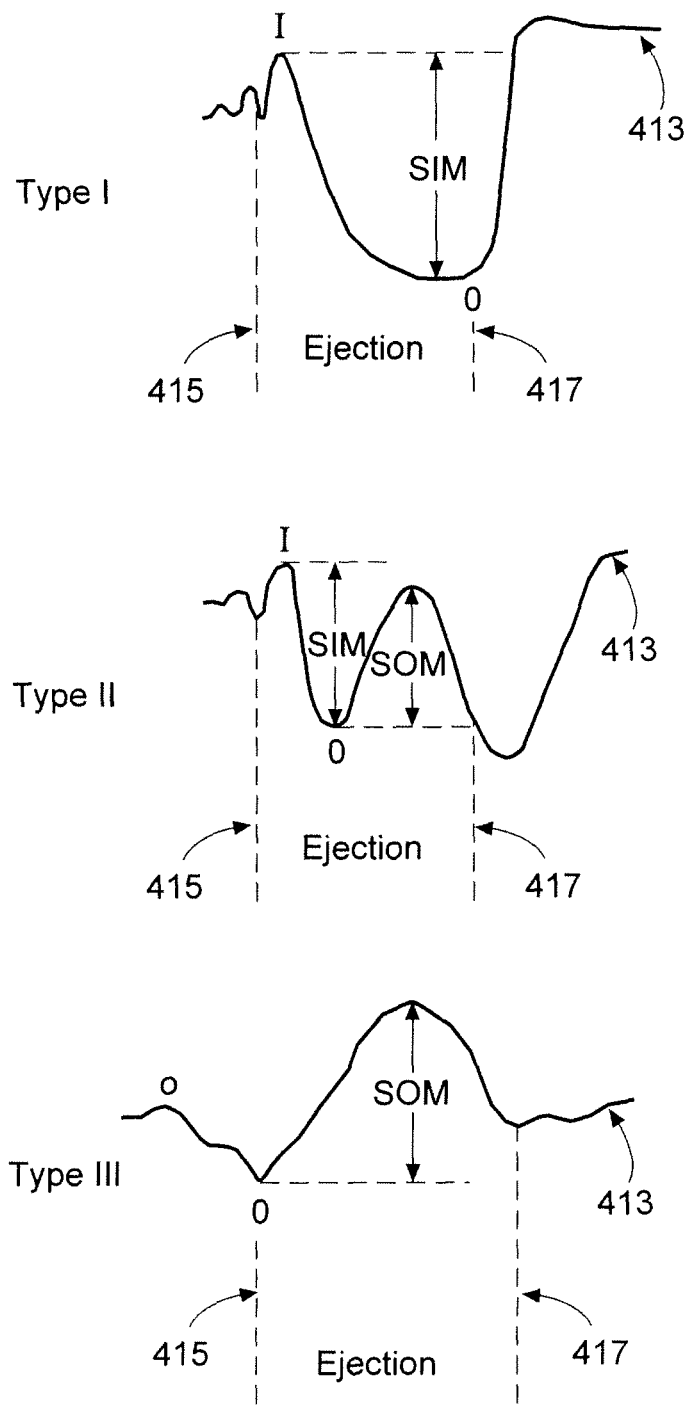

FIG. 4 illustrates a preferred method for manually or automatically determining the presence or absence of myocardial ischemia from the overall shape of the ventricular volume trace. Illustrated are three types, Types I, II, and III, of ventricular volume curves 413 from beginning of systole 415 to end of systole 417. Type I curves represent a normal morphology and is characterized by a largely monotonic downward motion (indicated by "SIM" or systolic inward motion) during systolic ejection reflecting cardiac contraction with inward wall motion away from the TCG sensor. The timing of the ejection portion of the waveform can be correlated with a concurrent ECG recording and should occur between the R-wave peak and T-wave peak (in the absence of artifact).

Abnormal patterns generally include "paradoxical" outward motion (toward the TCG sensor) occurring during all or part of systole. Such "paradoxical" outward motion occurs because a portion of the ventricular cannot normally contract because, e.g. it is shocked by acute loss of oxygen, or scarred from previous ischemic episodes, and the like. Types II and III represent samples of such abnormal TCG patterns (in the absence of artifact). Type II illustrates paradoxical systolic outward motion ((indicated by "SOM" or systolic outward motion) during a portion of normal systolic inward motion (SIN) or ejection. Here, the amplitudes of SIM and SOM are approximately equal, but in general, any detectable SOM is abnormal. This pattern has been termed 'dys-synergy'. Type III illustrates a severe abnormality where with holosystolic SOM and substantial absence of SIM. This pattern has been termed 'akinesis' or 'dyskinesis'. A variation of the Type III pattern also included in this category is systolic outward motion occurring for less than the entire period of ejection, but not preceded by inward motion during the first half of the ejection period; i.e., the inward motion was delayed and only occurred during the last half of ejection or during diastole.

After feature extraction 250, it is preferable to screen the extracted features 260 for artifacts. In one artifact screening method, the ventricular volume curve is examined and if key fiducial points, e.g., maxima and minima of the volume curve and of its first derivative, cannot be located, the current heart beat is noted. Next, a running baseline median average of N (preferably 10) consecutive beats is performed on the extracted features, and any heart beat having features with significant deviation from this running baseline is notes. Finally, features found in any cardiac cycles that have been so noted are excluded from analyses. In a further artifact screening method, periods of significant activity or motion can be excluded from analysis. Activity or motion can be sensed by one or more accelerometers, and periods of significant activity or motion can be excluded by excluding periods of significantly increase amplitude of the accelerometer signals.

The methods described herein may be programmed in any convenient computer language, such as assembly language, C, or C++, compiled into an executable form and stored on a computer readable medium for loading into the program memory of a programmable device. The present invention encompasses program products including such computer readable media on which the executable forms are recorded. The present invention further encompasses computer systems configured by such executable software to carry out the described methods.

Such systems can also be preferably coupled to other measurement instruments, for example, a stressor device such as a treadmill, in order to participate in more comprehensive testing. Such systems can also be preferably coupled to other clinical systems so that patients' cardiac activity can be monitored in real time. Such systems can receive TCG signal data from remote TCG sensors by means of wireless transmission of computer-readable medium. Further, such systems, or portions of such systems, can be miniaturized so that they may be carried by a monitored subject during their normal daily activities.

Methods and systems of the present invention have numerous uses in many areas of medicine, surgery, and related fields. Generally, the present invention can be used anywhere measurements of cardiac hemodynamic parameters, ventricular wall function, and the like are now of importance, and can be expected to enable new uses for cardiac monitoring. Particularly significant in this regard are its ease of use characteristics. For example, subject inconvenience is minimal; a monitored subject need only wear a garment including a TCG sensor. Subjects have full freedom; they need not be physically connected to any stationary monitoring equipment, since a local electronics modules that can be carried by can store or transmit TCG data, or even at rest in any specified position. Further, monitoring does not require trained medical personnel be present. Since it is unreasonable to describe all possible uses, the following description focuses without limitation on a number of exemplary uses. One of skill in the art will be able to apply the invention to uses that are not described.

First, the present invention can be used for screening, diagnosis, and treatment of coronary artery disease with both silent and symptomatic ischemia. For screening, it can be a useful addition to stress tests that seek to precipitate signs and symptoms of coronary artery disease and evaluate its severity. For diagnosis and treatment, subjects with known coronary artery disease, e.g., stable or unstable angina, can be continuously monitored even while they are performing the normal daily activities to assess the frequency and severity of transient ventricular wall motion abnormalities, whether they are associated with felt angina or other symptoms or whether they occur during symptom free periods. As described in connection with the actual example below, TCG-detected ventricular wall motion abnormalities can be expected to detect myocardial ischemia with greater sensitivity and specificity than elevated ST segment of other indicia recognized by ECG.

Figure 5A:
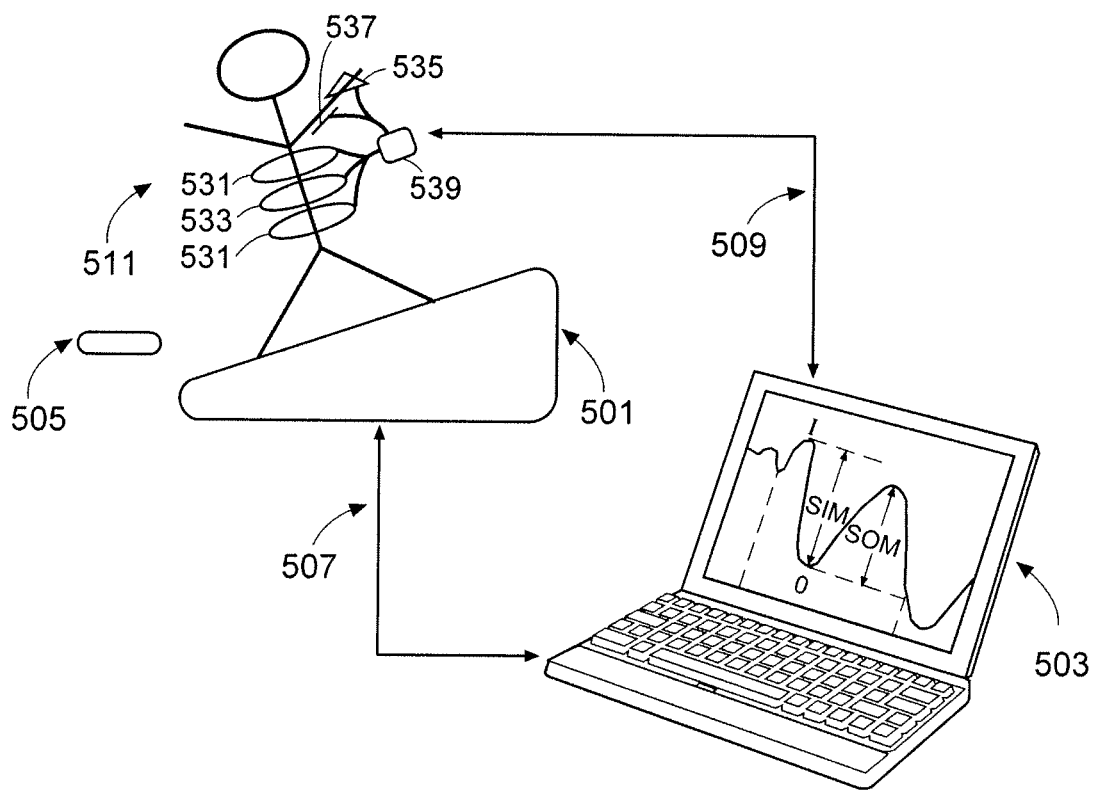
FIGS. 5A-B illustrate exemplary uses of the invention.

FIG. 5A illustrates an exemplary configuration of the invention suitable for screening for the presence and severity of myocardial ischemia, specifically, for recognizing paradoxical left ventricle wall motion induced by stress (a stress test). Here, subject 511 is wearing a monitoring garment (not illustrated) carrying a TCG sensor along with a number of other sensors. Loop 533 represents a TCG sensor based on IP technology positioned on the subject's mid-thorax at the level of the xiphoid process. Loops 531 are respiratory sensors based on IP technology positioned at the subject's rib cage and abdomen. Signals from these loops can be combined to provide a reliable tidal volume signal. ECG electrodes are represented at 537, and 535 represents further sensors such as a pulse oximeter, an accelerometer, and the like. Local electronics module 539 gathers sensor measurements for presentation 509 to analysis computer system 503. Data may be transferred between 539 and 503 on computer readable, over a wired link, or by a wireless link.

Cardiac stress may be caused by numerous factors: psychological stress resulting from driving in heavy traffic; physical stress resulting from exercise; pharmacologic resulting from certain medications. Here, physical stress is represented by treadmill 501 and pharmacological stress by mediation 505. From whatever cause, cardiac stress causes increased myocardial oxygen consumption which may trigger ischemia if blood flow is limited. Respiratory information can aid in assessing the level of myocardial oxygen consumption. Accelerometer information can aid in quantization of the level of exercise.

Analysis computer system 503 executes one or more of the above-described methods of this invention for extracting a ventricular wall signal from the input TCG sensor signal. It further extract some or all of the above-described cardiac indicia from the ventricular wall signal. Physiological sensor data is preferably provided to system 503 in real time, as by a wired or wireless link 509. In this case, system 503 can rapidly display the presence of absence of myocardial ischemia. Here, system 503 has detected and is displaying a Type II ventricular wall signal evidencing myocardial ischemia. System can then control the level of stress by providing a signal to controllable stressor 501. Thereby, the subject's safety can be better insured.

Preferably abnormal wall motion is detected and quantified automatically by system 503, at least, by classifying the ventricular wall signal as of Types I, II, or III. Alternatively, the ventricular wall signal can be manually evaluated by a trained individual. Preferably concurrent TCG and ECG signals are measured so that ECG analysis can enhance the diagnostic accuracy of the test procedure. For example, absence or presence and degree of ST segment deviation can be determined.

The configuration illustrated in FIG. 5A is specifically suitable for use in the clinic or the doctor's office for time limited subject testing. It should be understood, that similar system components can be configured for continuous or semi-continuous subject monitoring in an ambulatory context.

Next, the invention can be similarly used for subjects with congestive heart failure (CHF) of virtually any etiology. CHF leads to declining hemodynamic performance of the heart, which is directly measured by such indicia as SV, PER, TPER, and similar and can be visualized with the ventricular volume curve. For diagnosis, this invention can monitor a subject to assess the initial state of ventricular performance. During treatment, long term monitoring can, for example, help determine response to therapy, detect acute declines that may require hospitalization, track long term changes, and the like. This invention can perform such monitoring while subjects perform the normal daily activities.

The invention can also be used to monitor generally healthy subjects who are exposed to dangerous conditions or extreme stresses. For example, first responder and military personnel are at risk of injury, which can lead to blood loss, or dehydration, or other volume stress. Blood loss and dehydration can readily be recognized primarily from acute changes in stroke volume and cardiac output and also from changes in 50% FF and DT, all of which can be measured by this invention. Certain athletic endeavors, for example, rowing, cycling, mountain climbing, and similar, and aggressive athletic training can make extreme demands on the heart, and it can be prudent for persons engaging in such athletic activities to be monitored. This invention can provide such monitoring with minimal interference and little burden.

Second, this invention can be used in a wide range of different environments. Hospital patients can be semi-continuously or continuously monitored in regular setting without the need for intensive care unit conditions. Similarly, patients can be monitored in nursing homes or other care facilities. Also, cardiac function of patients in the clinic or the doctor's office can be routinely assessed using this invention. And importantly, this invention can be used by ambulatory subjects during their daily activities at home, at work, and elsewhere. As described, this invention can even be used by subjects on extreme conditions, or who are engaging in athletics, or similar. In all these environments, a local electronics module can store TCG data for later analysis and transmit it for real-time review, thus freeing a subject from wired links to data analysis locations.

Figure 5B:
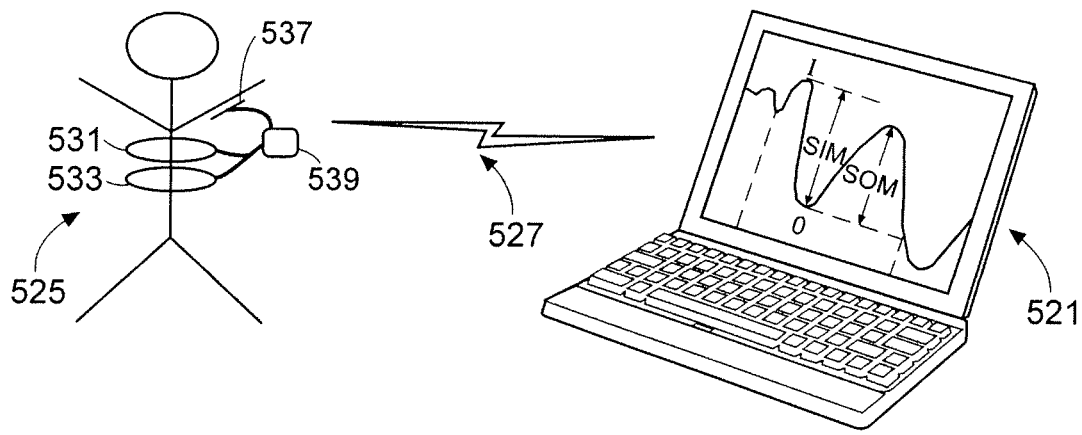

FIG. 5B illustrates an exemplary configuration of the invention suitable for cardiac monitoring in an ambulatory context. Here, subject 525 is also wearing a monitoring garment (not illustrated) carrying a more limited set of sensors (e.g., so as to be of lighter weight and less obtrusive to the subject). Sensors include TCG sensor 533 positioned on the subject's mid-thorax at the level of the xiphoid process. Single loop 531 is an IP-based respiratory sensor that can be combined to provide an indication of the subject's tidal volume. ECG electrodes are represented at 537. An accelerometer (not illustrated) is preferred. For the ambulatory context, local electronics module 539 preferably include sufficient processing capability at least to insure the gathered sensor measurements are of sufficient quality, and preferably to do sufficient analysis to determine the occurrence of cardiac alert conditions, e.g., the presence of myocardial ischemia.

Full analysis is generally performed on analysis computer system 521 which is not carried by the subject, but may be nearby or remote. In different embodiments, data can be transferred between 539 and 521 on computer readable or by a wireless link. For many continuous monitoring applications, it is generally sufficient to transfer data by computer readable medium for periodic, off-line review. For monitoring of acutely ill subjects, or of subjects in dangerous or stressful conditions, wireless data transmission for immediate, on-line review is generally preferred.

In most environments, but especially for ambulatory environments, concurrent accelerometer and/or respiration information is generally preferably to select appropriate periods review of TCG signals. Appropriate periods are generally stationary periods during or following significant stress. Such periods can be recognized when motion, as evidenced by accelerometer signals, is limited and breathing is temporarily stable after a period of stress evidenced by increased motion and an increasing or elevated respiration rate. Also, periods when either the respiration signal and/or the input TCG signal are not steady on average are preferably not analyzed. Additionally the timing of the systolic ejection portion of the curve relative to the R-wave and T-wave on the ECG may be used to further reject spurious cycles.

The invention can form the basis for numerous methods of treatment of cardiac conditions. Unique advantages of the present invention is that it can provide cardiac information over hours, days, or longer time periods while the subject is performing normal daily activities and/or is ambulatory. Generally, the methods of treatment would initially evaluate a subject by measuring cardiac parameters. On the basis of the measured cardiac parameters and other medical information, such as the history, lab tests, and the like, treatment can be recommended to the patient. Treatments for heart disease are well known. Medical treatments include dietary, exercise, pharmacologic interventions according to current practice known to practitioners of the medical arts. Surgical treatments include maintaining the patentcy of the coronary arteries by balloon procedures, stents, and the like, grafting vessel to bypass stenotic coronary arteries and are similarly well known the practitioner of the surgical arts. Methods of treatment preferably include further follow-up cardiac parameter evaluation, monitoring between formal re-evaluations, and so forth.

Such methods are particularly applicable to myocardial ischemic disease, congestive heart failure, and hypovolemia. In the latter, changes in the stroke volumes and the coronary output are of particular importance. Hypovolemia can occur in post-surgical patients, wounded military personnel, and others in dangerous or dehydrating environments.

The above-described uses and system configurations are not to be taken as limiting this invention, and additional uses and system configuration apparent to one of skill in the art are also within the present invention.

EXAMPLE

This example provides a clinical comparison and validation of the TCG against the cardiokymograph (CKG).

The CKG, first described in 1967 as the displacement cardiograph, is a noninvasive measurement device and method that provide an analog electrical signal representing cardiac wall motion. Specifically, non-invasive CKG measurements were made during actual stress tests (stress CKG) and observed wall motions of Types II and III were considered to be abnormal. Subsequently, the presence of absence of myocardial ischemia was determined by independent methods. The conclusion was that abnormal cardiac wall motion detected by the CKG reliably predicts coronary arterial disease. Stress CKG was 74% sensitive and 94% specific while stress ECG testing which was 59% sensitive and 69% specific. See, e.g., Silverberg et al., Noninvasive diagnosis of coronary artery disease: the cardiokymographic stress test., *Circulation.* 1980 Mar; 61 (3):579-89.

The TCG has been demonstrated in several clinical situations to produce waveforms that are highly similar to those produced by the CKG. Therefore, it can be concluded that the above published results concerning the success of CKG stress testing would also apply to TCG stress testing. In particular, in six healthy subjects, waveform shape and amplitude from a TCG sensor placed 3 cm caudad to the xiphoid process were compared to those produced by a CKG sensor in the same transverse plane as TCG and at the in the left mid-clavicular line in both the supine and prone postures. The CKG waveform (of Type I) was virtually identical to the TCG waveform (also of Type I). However, the CKG waveform was found to be sensitive to CKG sensor position. Movement of the CKG sensor a few cm to the left parasternal or left anterior axillary line often gave erroneous waveforms resembling cardiac dyskinetic motion or arteriovenous pulsations. In conclusion, in healthy subjects, first, waveforms from a well placed CKG sensor waveform are virtually identical to those recorded using TCG, and second, TCG waveforms are more reliable and more consistent from recording to recording.

Further, the TCG has been demonstrated to be able to distinguish subjects with otherwise known heart disease from subject without heart disease. In over 200 healthy subjects without significant heart disease, TCG always found a normal ventricular volume curve (Type I). But, in 25 cardiac patients who were otherwise know to have dyskinetic ventricular motion as measured with echocardiography, TCG found abnormal ventricular volume curves (Types II and III).

The invention described and claimed herein is not to be limited in scope by the preferred embodiments herein disclosed, since these embodiments are intended as illustrations of several aspects of the invention. Equivalent embodiments, various modifications and combinations of the invention, and the like, in addition to those shown and described herein, that will become apparent to those skilled in the art are also intended to fall within the scope of the appended claims. In the claims, the singular is to be understood as also including the plural, and "or" is to be understood as the inclusive or.

What is claimed is:

1. A method for determining cardiac parameters of a subject, comprising:
   receiving a signal from a thoracocardiograph (TCG) sensor, the signal being sensitive to positions and/or motions of an anterior chest wall of the subject, and the signal comprising a cardiac component, a respiratory component, and noise and/or artifact components;
   receiving one or more electrocardiogram (ECG) signals;
   filtering the received TCG signal such that one or more of the respiratory component and the noise and/or artifact components in the received TCG signal are reduced, the filtering comprising one or more of wavelet de-noising, non-linear filtering, and state space filtering;
   ensemble averaging the filtered TCG signal such that a respiratory component remaining in the filtered TCG signal is reduced, ensemble members being triggered by occurrence of one or more selected fiducial points determined in the ECG signal; and
   extracting parameters of cardiac functioning from the ensemble averaged signal.

2. The method of claim 1 wherein the extracted parameters of cardiac functioning comprise one or more of stroke volume, cardiac output, pre-ejection period, peak ejection rate, time to peak ejection rate, peak ejection rate divided by stroke volume, 50% filling fraction, peak filling rate, E/A ratio, deceleration time, indicators of a presence or absence of myocardial ischemia, and indicators of a severity of myocardial ischemia if present.

3. The method of claim 1 wherein the extracted parameters of cardiac functioning comprise indicators of dyskinetic ventricular wall motion, the method further comprising determining whether or not myocardial ischemia is likely to be present, and if present, determining a severity of ischemia in dependence on the indicators of dyskinetic motion.

4. The method of claim 1 further comprising determining whether or not hypovolemia is likely to be present by comparing current values of at least a stroke volume and cardiac output selected parameters with prior values of at least the stroke volume and cardiac output.

5. The method of claim 1 further comprising determining whether or not congestive heart failure (CHF) is likely to be present, and if present, determining a severity of the CHF in dependence on values of selected parameters.

6. The method of claim 1 wherein the fiducial points in the ECG signal selected for triggering the ensemble averaging comprise one or more of a P wave, a Q wave, a R wave, a S wave, and a T wave.

7. The method of claim 1 further comprising:
determining whether artifacts and/or noise are likely to be present in a signal during a period of time if either a fiducial point in an input signal that is expected to occur during the period cannot be recognized during the period, or a fiducial point occurs during the period at a time that is not expected; and
excluding all signals during the period if artifacts and/or noise are likely to be present in any signal.

8. The method of claim 7 wherein an expected fiducial point is selected from one or more of P, Q, R, S, and T waves in the ECG signal; the extracted parameters of cardiac functioning; and features of ventricular wall motion and a first derivative of the ventricular wall motion including maxima, minima, or zero crossings.

9. The method of claim 7 further comprising determining an expected occurrence time of a selected fiducial point during a period in dependence on a plurality of prior occurrence times of the selected fiducial point.

10. The method of claim 1, wherein the filtering comprises the wavelet de-noising.

11. The method of claim 1, wherein the filtering comprises the state space filtering.

12. The method of claim 1, wherein the filtering comprises the non-linear filtering.

* * * * *

UNITED STATES PATENT AND TRADEMARK OFFICE
CERTIFICATE OF CORRECTION

| | | |
|---|---|---|
| PATENT NO. | : 8,790,272 B2 | Page 1 of 1 |
| APPLICATION NO. | : 11/753337 | |
| DATED | : July 29, 2014 | |
| INVENTOR(S) | : Marvin Sackner et al. | |

It is certified that error appears in the above-identified patent and that said Letters Patent is hereby corrected as shown below:

Title page, Item (63) Related U.S. Application Data, lines 4-6, replace "6,783,498, application No. 11/753,337, which is a continuation-in-part" with -- 6,783,498. Continuation-in-part --.

Title page, Item (57) Abstract, line 12, replace "thefiltered" with --the filtered--

Signed and Sealed this
Sixteenth Day of December, 2014

Michelle K. Lee
*Deputy Director of the United States Patent and Trademark Office*